US010249833B2

(12) United States Patent
Gao et al.

(10) Patent No.: US 10,249,833 B2
(45) Date of Patent: Apr. 2, 2019

(54) PHTHALOCYANINE COMPOUND AND SYNTHESIS METHOD AND USE THEREOF

(71) Applicant: BOE TECHNOLOGY GROUP CO., LTD., Beijing (CN)

(72) Inventors: Xue Gao, Beijing (CN); Fei Liu, Beijing (CN); Can Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/225,244

(22) Filed: Aug. 1, 2016

(65) Prior Publication Data

US 2017/0256725 A1    Sep. 7, 2017

(30) Foreign Application Priority Data

Mar. 2, 2016    (CN) .......................... 2016 1 0118563

(51) Int. Cl.
*H01L 51/00*    (2006.01)
*C07F 15/04*    (2006.01)
(Continued)

(52) U.S. Cl.
CPC .......... *H01L 51/0078* (2013.01); *C07F 1/005* (2013.01); *C07F 1/08* (2013.01);
(Continued)

(58) Field of Classification Search
CPC .............. H01L 51/0078; H01L 51/009; H01L 51/0003; H01L 51/0007; H01L 51/0558;
(Continued)

(56) References Cited

U.S. PATENT DOCUMENTS

2008/0055443 A1* 3/2008 Okamoto .......... H01L 27/14647
348/298

FOREIGN PATENT DOCUMENTS

CN    102216397 A    10/2011
CN    102850359 A    1/2013
(Continued)

OTHER PUBLICATIONS

Sergey G. Makarov, Olga N. Suvorova, Christian Litwinski, Eugeny A. Ermilov, Beate Röder, Olga Tsaryova, Thomas Dülcks, and Dieter Wöhrle, Eur. J. Inorg. Chem. 2007, 546-552, 2007 Wiley-VCH Verlag 546 GmbH & Co. KGaA, Weinheim.*
(Continued)

*Primary Examiner* — Bijan Ahvazi

(74) *Attorney, Agent, or Firm* — Kinney & Lange, P.A.

(57) ABSTRACT

The invention relates to a phthalocyanine compound, which has a structure as represented by Formula I, wherein A represents a transition metal or a rare earth metal; R1 represents a phenyl group, a naphthyl group, or a $C_4$-$C_{16}$ n-alkyl group. The aromatic phthalocyanine compound having the structure of Formula I provided in the invention contains a transition metal or a rare earth metal, and introduces a peripheral substituent into a linearly extended π-conjugated system. It is relatively stabler at 400° C. or less and will be easily evaporated in vacuum to form a uniform thin film, and has good thermal stability, high chemical stability, and high mobility. The organic semiconductor device has the features of relatively fast on-off speed, relatively high on-off ratio, and strong reliability.

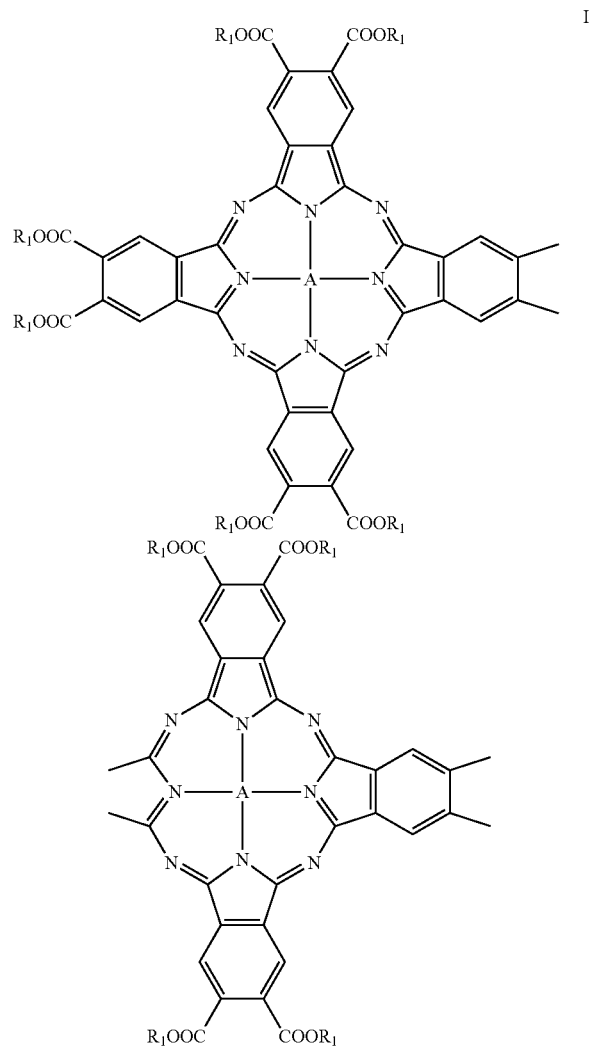

(Continued)

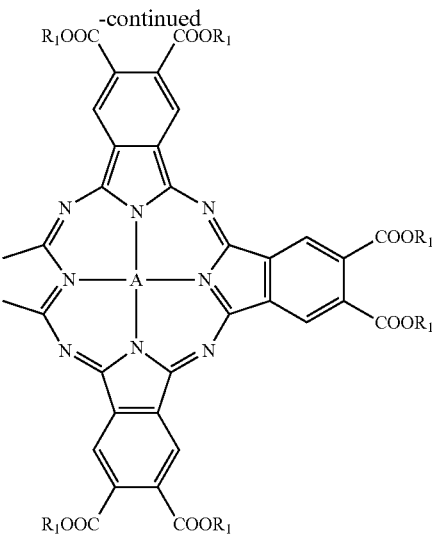

6 Claims, No Drawings

(51) Int. Cl.
*C07F 1/08* (2006.01)
*C07F 3/06* (2006.01)
*C07F 15/06* (2006.01)
*C07F 1/00* (2006.01)
*C09B 47/067* (2006.01)
*H01L 51/05* (2006.01)

(52) U.S. Cl.
CPC .............. *C07F 3/06* (2013.01); *C07F 15/045* (2013.01); *C07F 15/065* (2013.01); *C09B 47/0678* (2013.01); *H01L 51/009* (2013.01); *H01L 51/0003* (2013.01); *H01L 51/0007* (2013.01); *H01L 51/0558* (2013.01)

(58) Field of Classification Search
CPC .. C07F 1/08; C07F 3/06; C07F 15/045; C07F 15/065
USPC ...................... 252/582, 587; 257/40; 524/88; 540/122, 137, 140
See application file for complete search history.

(56) References Cited

FOREIGN PATENT DOCUMENTS

JP 64-045386 2/1989
JP H1149973 A 2/1999

OTHER PUBLICATIONS

Xueying Wang, Yuexing Zhang, Xuan Sun, Yongzhong Bian, Changqin Ma, and Jianzhuang Jiang, 2,3,9,10,16,17,24,25-Octakis(octyloxycarbonyl)phthalocyanines. Synthesis, Spectroscopic, and Electrochemical Characteristics,Inorganic Chemistry, vol. 46, No. 17, 2007,© 2007 American Chemical Society.*
First Chinese Office Action, for Chinese Patent Application No. 201610118563.X, dated Apr. 27, 2017, 13 pages.
Wang, Xueying, "2,3,9,10,16,17,24,25-Octakis(octyloxycarbonyl)phthalocyanines. Synthesis, Spectroscopic, and Electrochemical Characteristics", Inorganic Chemistry Article, published Jul. 27, 2007, 6 pages.
Makarov, Sergey G., "Linear and Rectangular Trinuclear Phthalocyanines", European Journal of Inorganic Chemistry, 2007, 7 pages.
Second Chinese Office Action, for Chinese Patent Application No. 201610118563.X, dated Nov. 28, 2017.

* cited by examiner

PHTHALOCYANINE COMPOUND AND SYNTHESIS METHOD AND USE THEREOF

TECHNICAL FIELD

The invention relates to a phthalocyanine compound and the synthesis method and use thereof, and belongs to the field of organic semiconductor materials.

BACKGROUND ART

In recent years, organic field effect transistors (OFETs) composed of conjugated polymers, oligomers, or small organic molecules have some unique advantages and thus much attention has been paid thereto by researchers. They can be processed at room temperature, bendable, and low-cost, and can be subjected to mass production. They can be used in drive circuits of flat panel displays, as memory elements for transaction cards and identification recognizers, smart cards, etc.

Since 1987 when OFETs were reported, the performances of OFETs have been improved to some extent, and there is a great progress in the study on organic semiconductor materials. However, the performances in terms of thermal stability, chemical stability, mobility, etc., are still to be further improved.

SUMMARY OF THE INVENTION

One embodiment of the invention provides a phthalocyanine compound, having a structure as represented by Formula I,

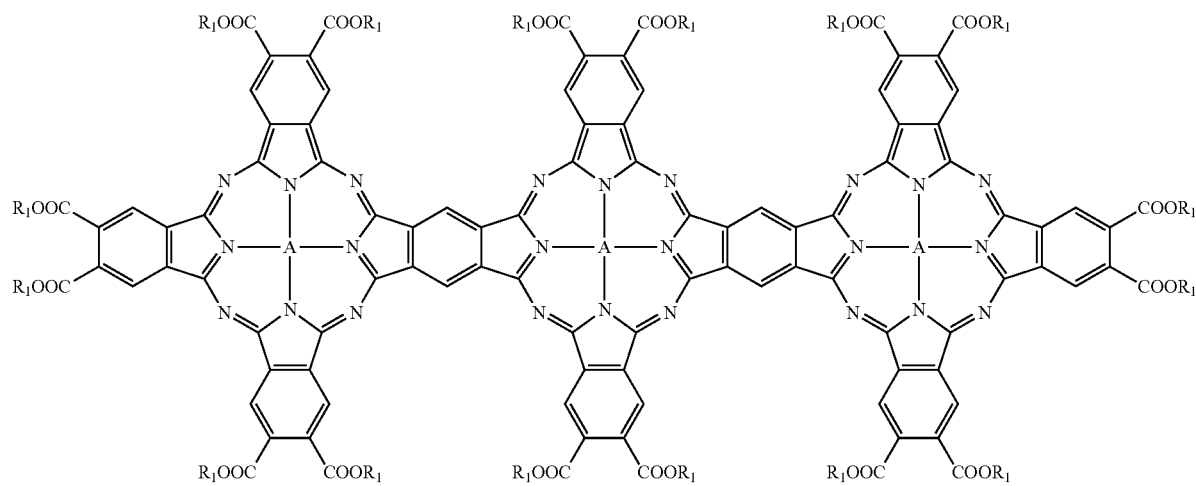

I wherein A represents a transition metal or a rare earth metal; R1 represents a phenyl group, a naphthyl group, or a $C_4$-$C_{16}$ n-alkyl group.

Preferably, A is selected from Ni, Zn, Cu, Co, Fe, Mn, Eu, or Lu.

More preferably, A is selected from Cu.

Preferably, R1 is selected from —$C_4H_9$ or —$C_8H_{17}$.

As one of preferred embodiments of the invention, said phthalocyanine compound has a structure below.

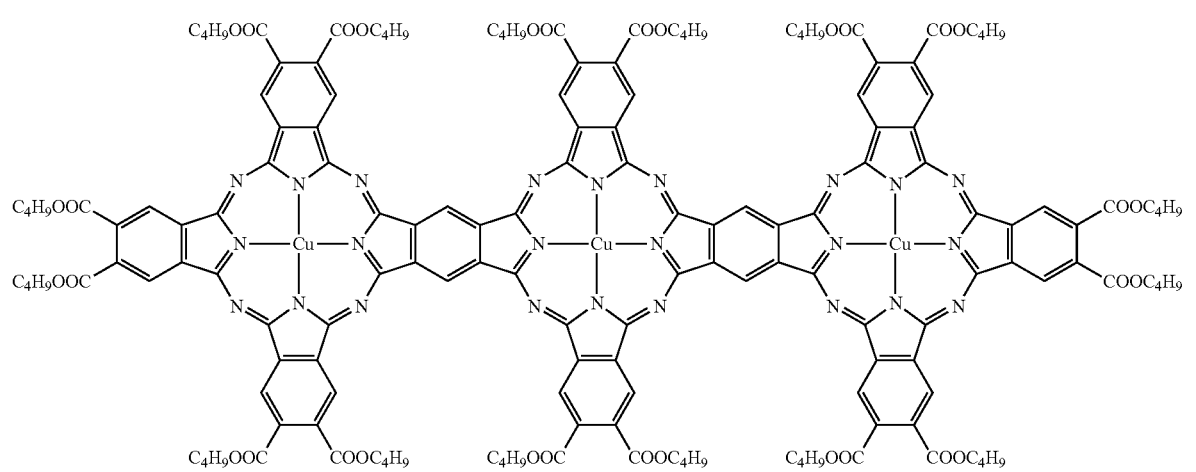

1

Another embodiment of the invention provides a synthesis method for a phthalocyanine compound, comprising the steps of:

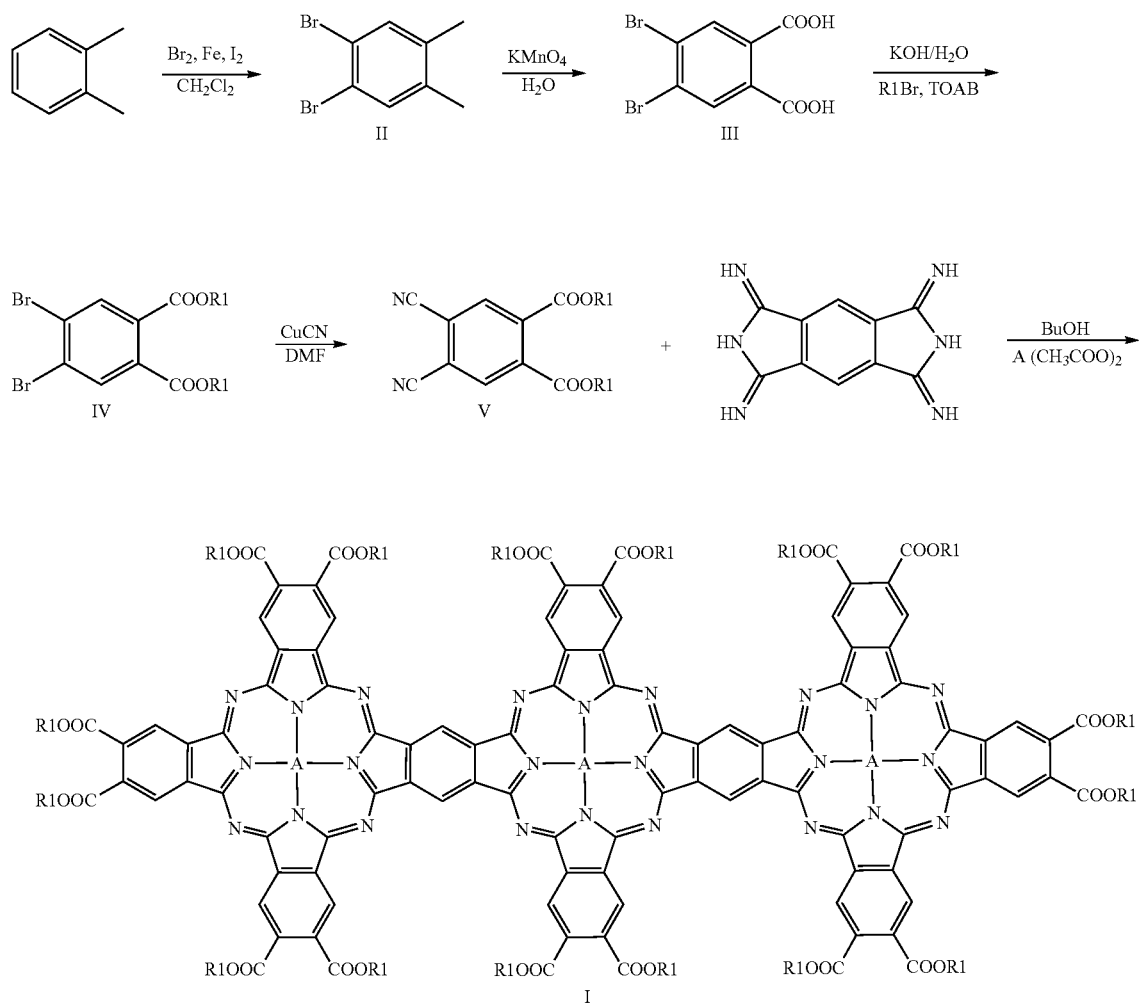

reacting o-xylene with liquid bromine to produce a compound II of 4,5-dibromo-o-xylene;

producing a compound III of 4,5-dibromo-o-phthalic acid from 4,5-dibromo-o-xylene under the action of potassium permanganate;

reacting 4,5-dibromo-o-phthalic acid with R1Br under the action of potassium hydroxide and a catalyst of tetraoctylammonium bromide to produce a compound IV;

reacting the compound IV with cuprous cyanide to produce a compound V; and reacting the compound V with bis(diiminoisoindoline) and $A(CH_3COO)_2$ to produce a phthalocyanine compound having a structure as represented by Formula I;

wherein the meanings of A and R1 are as described above.

Still another embodiment of the invention provides the use of the phthalocyanine compound having the structure represented by Formula I in an organic semiconductor material.

Still another embodiment of the invention provides an organic semiconductor device, comprising an electrode, an insulating layer, and a semiconductor layer, wherein said semiconductor layer comprises at least one organic layer, and said organic layer comprises at least the compound having the structure represented by Formula I. Said electrode comprises a gate electrode, a source electrode, and a drain electrode.

Still another embodiment of the invention provides a method for producing an organic semiconductor device, wherein said organic layer can be prepared by using conventional methods in the art, such as solvent evaporation self-assembly, quasi-Langmuir-Shäfer (QLS) method, or drop coating method.

DESCRIPTION OF EMBODIMENTS

In order to obtain a semiconductor material having good thermal stability, high chemical stability, and high mobility, one embodiment of the invention provides a phthalocyanine compound of Formula I, which has excellent performances in respective aspects mentioned above and can be used in the preparation of OFETs:

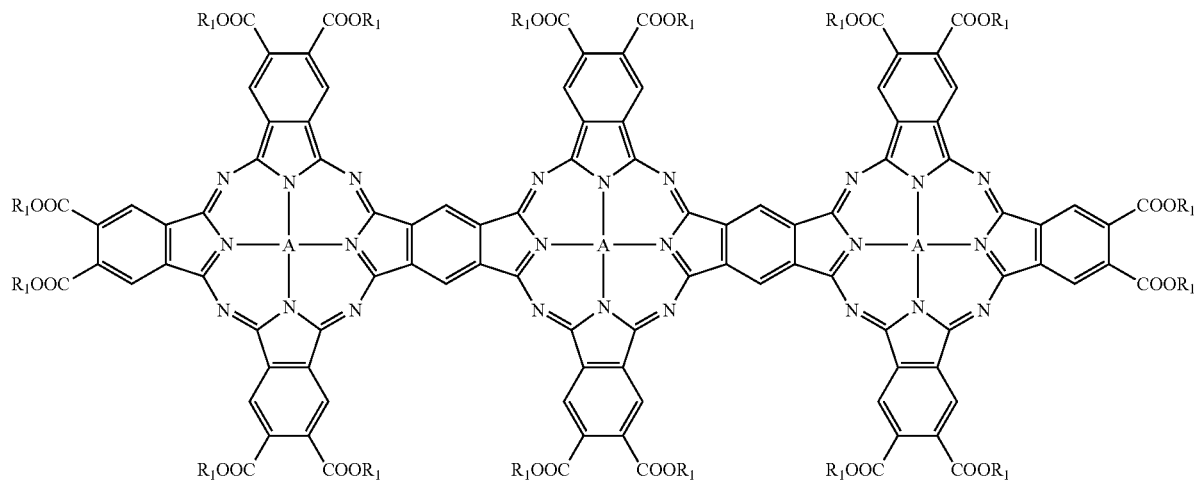

wherein A represents a transition metal or a rare earth metal; R1 represents a phenyl group, a naphthyl group, or a $C_4$-$C_{16}$ n-alkyl group.

Furthermore, said A may be selected from transition metals, such as Ni, Zn, Cu, Co, Fe, Mn, etc., or rare earth metals, such as Eu, Lu, etc.; and it is further confirmed that when A is Cu, with respect to other metals, the phthalocyanine compound can exhibit better properties such as electron mobility, etc., and it is favorable to improve thermal stability, chemical stability, and mobility of the phthalocyanine compound.

In the process of study, it is found that higher alcohols obtained by hydrolysis typically have poor solubility and relatively high boiling points and tend to affect subsequent purification processing. Therefore, said R1 in the invention is preferably —$C_4H_9$ and —$C_8H_{17}$.

The phthalocyanine compound described in the embodiment of the invention has not only stable electrochemical properties, but also a π-bond conjugated system. The axial direction of the overlapped π bond may be consistent with the direction of the shortest distance between the source electrode and the drain electrode, which is more favorable to the transport of carriers, and there are advantages of high mobility, low intrinsic conductivity, etc. Further, the switching speed of OFET devices is ensured and the drain current of OFET devices are reduced as much as possible, so that the on-off ratio of OFET devices is improved and the reliability of OFET devices is increased.

The synthesis method described in the embodiment of the invention has features, such as simple operation and low cost, and is more suitable for industrial production.

As an organic semiconductor material, the phthalocyanine compound having the structure represented by Formula I has good thermal stability, high chemical stability, and high mobility.

The organic semiconductor device according to the embodiment of the invention has features, such as relatively fast switching speed, relatively high on-off ratio, and high reliability.

By solvent evaporation self-assembly, quasi-Langmuir-Shäfer (QLS) method, or drop coating method, a thin film of an organic layer is deposited on a substrate, such as ITO/glass, silica, or the like, an organic semiconductor device is produced by mounting a gold electrode, etc., and tests are performed on properties, such as electron mobility, etc.

The aromatic phthalocyanine compound having the structure of Formula I provided in the embodiment of the invention contains a transition metal or a rare earth metal, and introduces a peripheral substituent into a linearly extended π-conjugated system. It is relatively stabler at 400° C. or less and will be easily evaporated in vacuum to form a uniform thin film, and has good thermal stability, high chemical stability, and high mobility. The organic semiconductor device has the features of relatively fast switching speed, relatively high on-off ratio, and high reliability.

The preparation and use of the phthalocyanine compound of Formula I will be further illustrated below.

Unless particularly described, raw materials and intermediates used herein are all commercially available products.

Example 1

This Example provided a phthalocyanine compound, which was prepared by the following method:

Synthesis of 4,5-dibromo-o-xylene (Compound II)

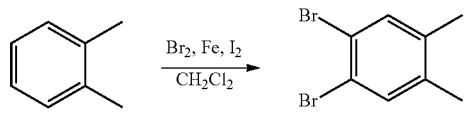

24 ml (0.2 mol) of o-xylene was dissolved in 30 ml of dried dichloromethane, and 2.5 g (10 mmol) of iodine and 0.6 g (10 mmol) of reduced iron powder were added with stirring. The mixture was cooled to 0° C. with an ice bath. 20.5 ml (0.4 mol) of liquid bromine was further dissolved in 10 ml of dried dichloromethane, and this solution was uniformly and slowly dropped into the reaction mixture with a dropping funnel over six hours, while hydrogen bromide gas evolved was absorbed by a funnel inverting on a 10% sodium hydroxide solution. The reaction was continuously stirred at 0° C. for 38 hours, and then stirring was continued at room temperature for 6 hours. First, the reaction mixture was washed with a 5% sodium hydroxide solution until becoming colorless, and then the organic layer was separated; thereafter, it was washed with a 5% sodium bisulfite solution until becoming neutral, and then the organic layer was separated. Anhydrous sodium sulfate was added for drying. Suction filtration was performed after standing overnight, and the filtrate was subjected to reduced-pressure distillation on a rotary evaporator to obtain a brownish oily liquid. To the liquid, methanol having a volume 8-10 times as great as the volume of the liquid was added. They were heated with stirring to be boiled, and then the stirring was stopped and the temperature was reduced to 0° C. for recrystallization. 32.7 g of transparent needle-like crystal was obtained, with a yield of 62%.

Result of product analysis: melting point of 88° C.; $^1$H nuclear magnetic resonance (300 MHz): (CDCl$_3$) 7.37 (single peak, 2H, benzene ring), 2.18 (single peak, 6H, methyl); MALDI.TOF mass spectrometry: molecular ion peak 264.0, theoretical value of 264.0; elemental analysis: C$_8$H$_8$Br$_2$: theoretical value: C, 36.40%; H, 3.05%. Found: C, 36.36%; H, 2.92%.

(2) Synthesis of 4,5-dibromo phthalic Acid (Compound III)

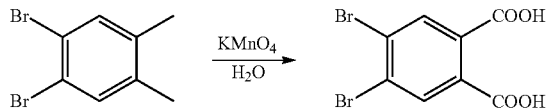

6.5 g (0.025 mol) of 4,5-dibromo-o-xylene was finely ground and added to 200 ml of water to form a suspension with stirring, which was heated to be boiled. 15.8 g (0.1 mol) of potassium permanganate powder was equally divided into three equal portions, which were added to the reaction mixture once every 2 hours, with the reaction performed for 6 hours in total. The reaction mixture was cooled to room temperature, and sodium bisulfite was slowly added thereto to reduce remaining potassium permanganate, until purple red completely disappeared. Potassium hydroxide was added to the reaction mixture to adjust the pH value to 12 or more. The reaction mixture was subjected to suction filtration with a Buchner funnel to obtain a clear colorless filtrate, which was a potassium 4,5-dibromo-o-phthalate solution. The filter residue was washed with a 1% KOH solution twice, and the washing liquid was incorporated to the filtrate. Concentrated hydrochloric acid (18M) was slowly added to the filtrate dropwise for acidification until the pH is approximately equal to 2, and a large amount of white flocculent 4,5-dibromo-o-phthalic acid precipitate was separated out. Suction filtration was performed with a Buchner funnel, and the filter cake was washed with a small amount of 1% hydrochloric acid solution and was then placed in a drier with silica gel-self indicator for drying. 7.3 g of a white glossy solid was obtained, with a yield of 90%. Result of product analysis: melting point of 300 degrees or more; since the product was insoluble in normal organic solvents, no satisfying nuclear magnetic resonance result was obtained, and the result of elemental analysis had a slightly large error due to difficult purification; MALDI-ToF mass spectrometry: molecular ion peak m/z 323.2, [M]+ theoretical value 323.9; elemental analysis: C$_8$H$_4$O$_4$Br$_2$: theoretical value: C, 29.66%; H, 1.24%. Found: C, 27.73%; H, 1.20%.

(3) Synthesis of butyl 4,5-dibromo-o-phthalate (Compound IV)

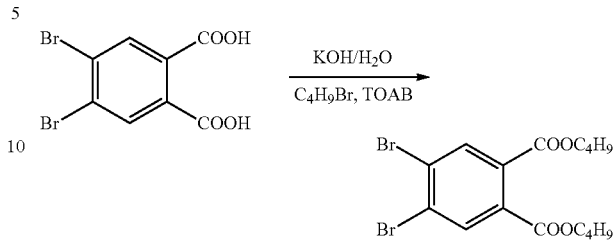

3.24 g (0.01 mol) of 4,5-dibromo-o-phthalic acid and 1.12 g (0.02 mol) of potassium hydroxide were added to 100 ml of distilled water, and were completely dissolved by stirring. In order to accelerate the process of dissolution, heating could be properly performed in the process of stirring. 3.86 g (0.01 mol) of 1-bromobutane and 2 g of tetraoctylammonium bromide (TOAB) as a phase transfer catalyst were added to the solution. The reaction mixture was heated to 100° C., refluxed with stirring under the protection of nitrogen gas for 4 hours, and then cooled to room temperature. The reacting liquid was extracted with toluene (3 times, 30 ml for each time). Organic phases were combined and anhydrous magnesium sulfate was added thereto for drying. Suction filtration was performed with a Buchner funnel after standing overnight, and the filtrate was subjected to reduced-pressure distillation on a rotary evaporator to obtain a light yellow oily liquid. With chloroform as an eluent, the product was purified by a silica gel chromatographic column, and ultraviolet-developed bands were collected under an ultraviolet lamp at a wavelength of 254 nm. 4.22 g of pure butyl 4,5-dibromo-o-phthalate was finally obtained after two times of purification, with a yield of 77%.

(4) Synthesis of 4,5-dicarbonylbutoxy-o-dicyano benzene (Compound V)

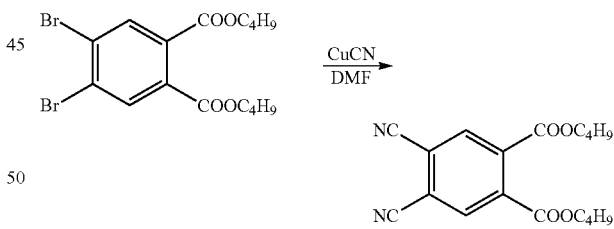

5.48 g (0.01 mol) of butyl ester of 4,5-dibromo-o-phthalic acid and 1.79 g (0.02 mol) of cuprous cyanide were added to 100 ml of DMF, and the reaction mixture was refluxed with stirring and heating under the protection of nitrogen gas for 2 hours. After cooling to room temperature, the reaction mixture was poured into 200 ml of distilled water and was extracted with toluene (3 times, 35 ml for each time). Organic phases were combined, and washed with distilled water for several times (five to ten times), so as to remove residual fine granular cuprous bromide. Anhydrous magnesium sulfate was added to the washed toluene solution for drying. Suction filtration was performed with a Buchner funnel after standing overnight, and the solvent was removed by reduced-pressure distillation to obtain a brown oily liquid. With a chloroform/n-hexane mixed solution at a volume ratio of 1:1 as an eluent, the product was purified by a silica gel chromatographic column, and the first ultraviolet-developed band was first collected under an ultraviolet lamp at a wavelength of 254 nm, which was incompletely reacted butyl 4-bromo-5-cyano-o-phthalate; and the second ultraviolet-developed band was then collected, which was the product of interest, 4,5-dicarbonylbutoxy-o-dicyano benzene. After two times of purification, the solution was dried by evaporation to obtain white powder. The product was dissolved in a small amount of chloroform and recrystallized in a large amount of methanol to obtain 1.19 g of white crystal, with a yield of 27%.

(5) Synthesis of the Product of Interest (Compound I)

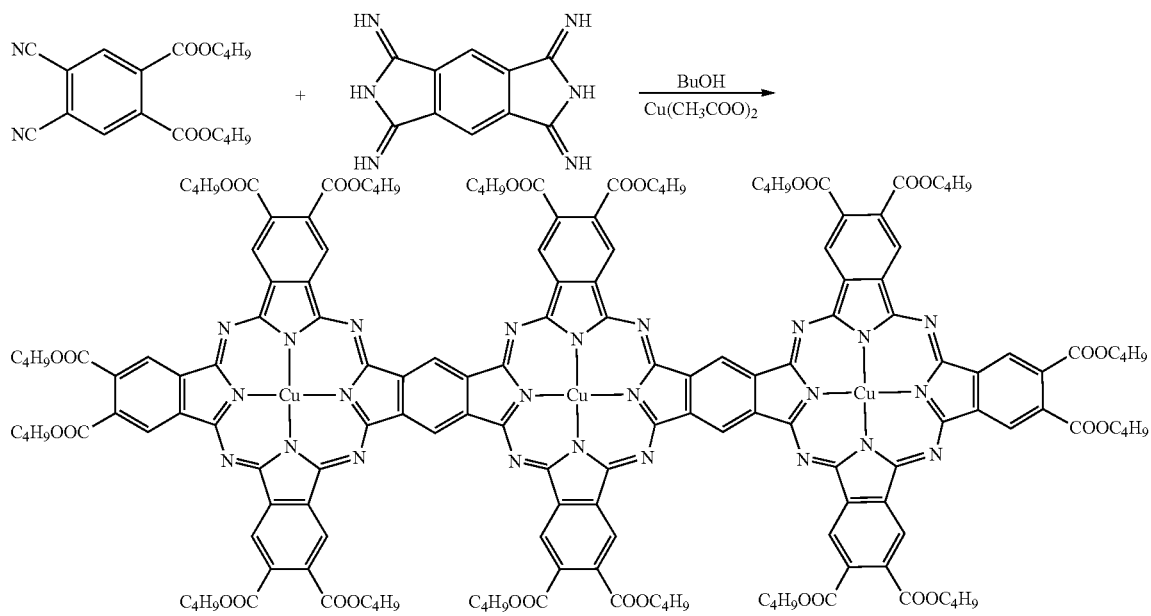

328 mg (1 mmol) of 4,5-dicarbonylbutoxy-o-dicyano benzene, 26 mg (0.125 mmol) of bis(diiminoisoindoline), and $Cu(CH_3COO)_2$ (690 mg, 1.88 mmol) were added to 8 ml of n-butanol, and the reactants were heated to reflux in a nitrogen atmosphere for 24 h. After cooling to room temperature, the solvent was drawn off. The residue was added to trichloromethane and dissolved, and the product compound I was obtained by using trichloromethane and n-hexane as eluting agents.

Upon detection, the resultant product of interest compound I had thermal stability, high chemical stability, and high mobility.

Example 2

By replacing $Cu(CH_3COO)_2$ in step (5) of Example 1 with $Ni(CH_3COO)_2$, $Co(CH_3COO)_2$, or $Zn(CH_3COO)_2$, it was possible to prepare the same serious of corresponding compounds of Ni, Co, or Zn having the same substituent.

Example 3

By replacing 1-bromobutane in step (3) of Example 1 with 1-bromooctane, bromophenyl, or bromonaphthyl, it was possible to prepare the same serious of substitutions having a central metal of copper and corresponding substituents of an octyl ester group, a phenyl ester group, or a naphthyl ester group.

Example 4 Organic Semiconductor Device

This Example provided an organic semiconductor device, comprising an electrode, an insulating layer, and a semiconductor layer; wherein said semiconductor layer comprised at least one organic layer, and said organic layer was produced from the phthalocyanine compound in Example 1.

Said organic semiconductor device is prepared by using phase transfer method, which was, in particular, as follows: a small amount of chloroform solution (about 1 mM) containing the phthalocyanine compound 1 (5-125 microliters) obtained in Example 1 was rapidly injected into a large amount of methanol (25 mL) with a microsyringe respectively, and gentle stirring was performed with a syringe, and then precipitated nanostructures were withdrawn from the solution. Throughout the processes of the experiments, temperature, concentration, and injection speed were different and can be adjusted according to practical situations, but the results all exhibited good repeatability.

The ultraviolet spectrum of said organic semiconductor device may be measured by dispersing in methanol. Photographs TEM and SEM can be taken by dropping samples on pure carbon films. When SEM was carried out, gold with a thickness of 1-2 nm was sputtered on the surface of the sample. A drop of prepared sample was dropped onto a silica substrate, and after methanol volatilized, a gold electrode was thermally evaporated onto a nanomaterial by using a gold wire as a template. The distance between two electrodes was 55 micrometers, and the current-voltage property was measured by a Keithley4200 semiconductor tester at room temperature.

Upon detection, the resultant organic semiconductor device had a mobility increased by 10% and a drain current reduced by 2%, and the on-off ratio of the OFET device was increased by 5%.

At the meanwhile, the phthalocyanine compounds obtained in Examples 2-3 were tested by using the organic semiconductor device prepared by the method above, and the results thereof were substantially consistent with that of Example 4.

Although the invention has been exhaustively described hereinbefore by using general descriptions and specific embodiments, some modifications and improvements may be made thereto based on the invention, which is apparent to the person skilled in the art. Therefore, these modifications or improvements made on the basis of not departing from the spirit of the invention all belong to the scope sought to be protected by the invention.

What is claimed is:

1. A synthesis method for a phthalocyanine compound consisting of a structure as represented by Formula I below,

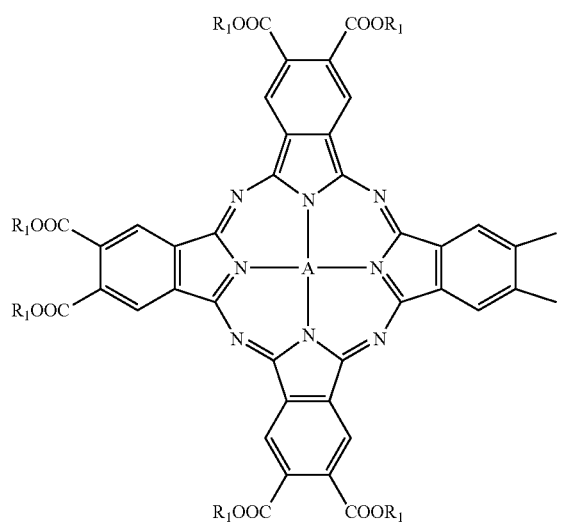

I

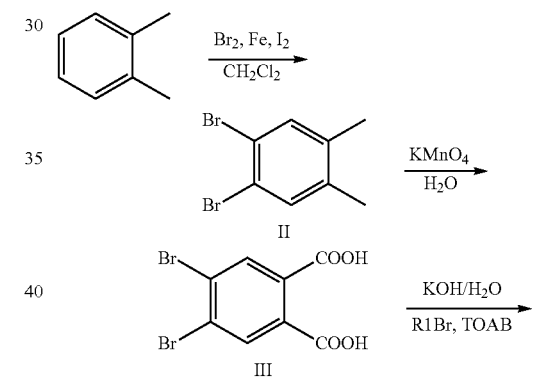

wherein A represents a transition metal or a rare earth metal, and R1 represents a phenyl group, a naphthyl group, or a $C_4$-$C_{16}$ n-alkyl group, wherein the synthesis method comprises the steps of:

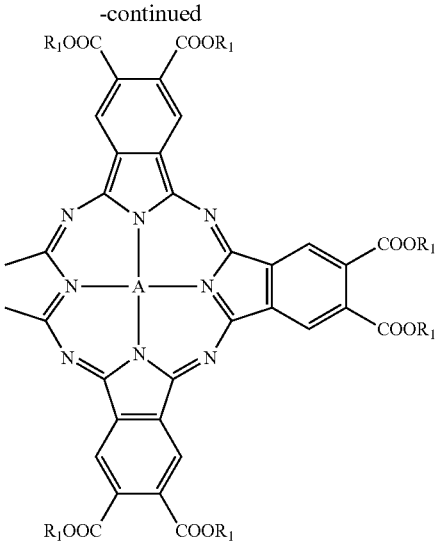

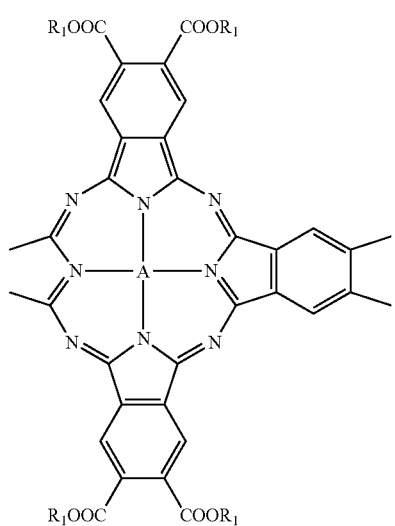

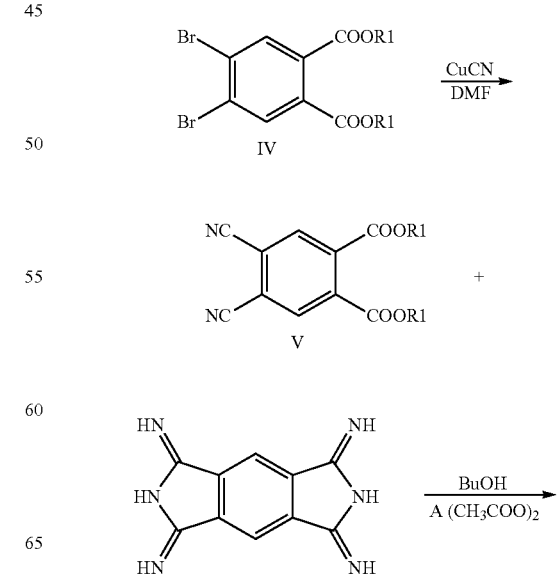

-continued

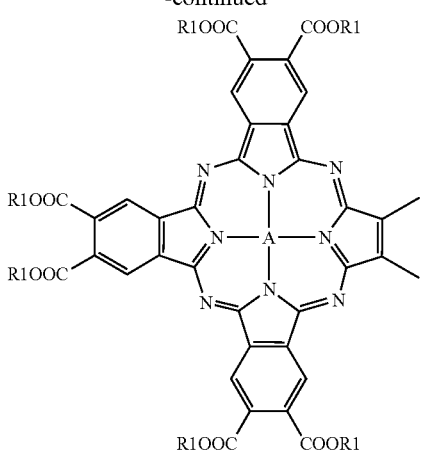

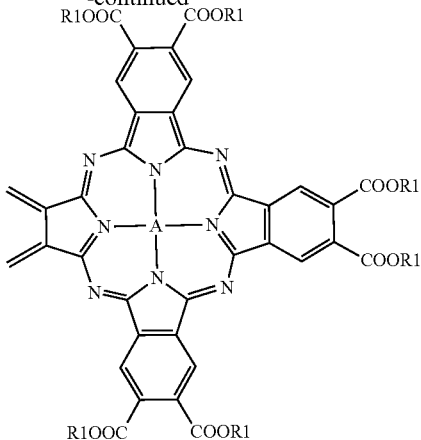

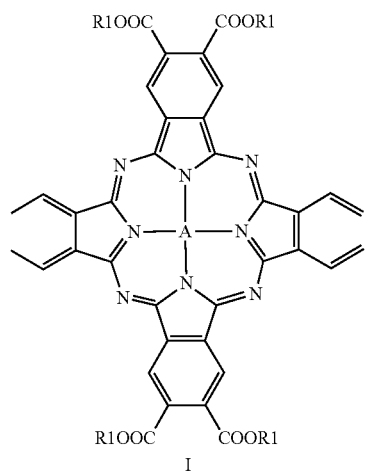

I (1) reacting o-xylene with liquid bromine to produce a compound II of 4,5-dibromo-o-xylene;
(2) producing a compound III of 4,5-dibromo-o-phthalic acid from 4,5-dibromo-o-xylene under the action of potassium permanganate;
(3) reacting 4,5-dibromo-o-phthalic acid with R1Br in the presence of potassium hydroxide and a catalyst of tetraoctylammonium bromide to produce a compound IV;
(4) reacting the compound IV with cuprous cyanide to produce a compound V; and
(5) mixing and reacting the compound V with bis(diiminoisoindoline) and $A(CH_3COO)_2$ to produce a phthalocyanine compound consisting of a structure as represented by Formula I.

2. The synthesis method according to claim 1, wherein A is selected from the group consisting of Ni, Zn, Cu, Co, Fe, Mn, Eu, and Lu.

3. The synthesis method according to claim 2, wherein A is Cu.

4. The synthesis method according to claim 1, wherein R1 is selected from the group consisting of —$C_4H_9$ and —$C_8H_{17}$.

5. The synthesis method according to claim 1, wherein said phthalocyanine compound has a structure as below:

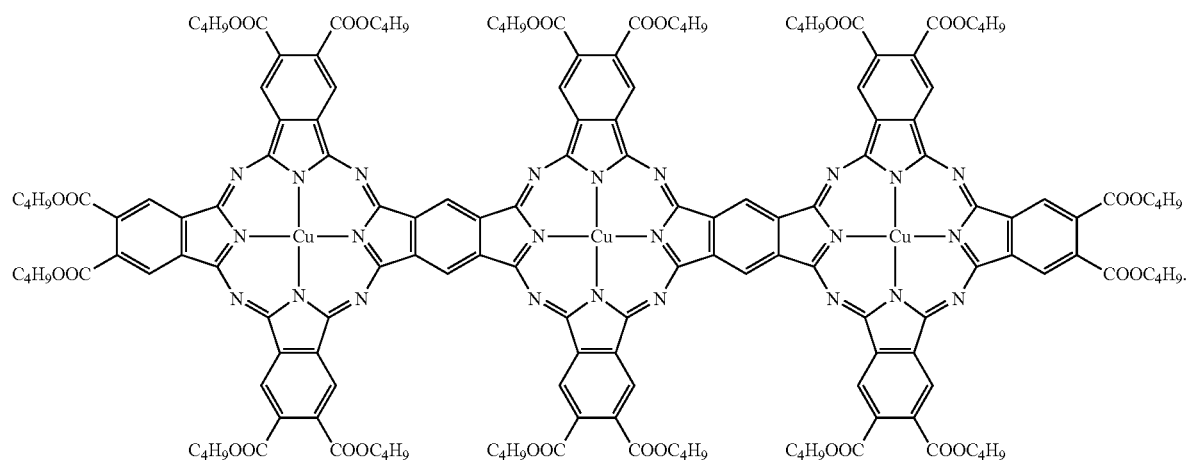

6. The synthesis method according to claim 1, wherein the step (5) comprises:
- adding compounds consisting of the compound V, bis (diiminoisoindoline) and $A(CH_3COO)_2$ to n-butanol, so as to form a mixture,
- heating the mixture to reflux, so as to obtain a resultant,
- cooling the resultant to room temperature,
- drawing off the solvent, so as to obtain a residue,
- adding the residue to trichloromethane, and
- performing elution by using trichloromethane and n hexane, so as to obtain the compound I.

* * * * *

UNITED STATES PATENT AND TRADEMARK OFFICE
CERTIFICATE OF CORRECTION

PATENT NO. : 10,249,833 B2
APPLICATION NO. : 15/225244
DATED : April 2, 2019
INVENTOR(S) : Xue Gao, Fei Liu and Can Zhang It is certified that error appears in the above-identified patent and that said Letters Patent is hereby corrected as shown below:

On the Title Page

Column 2, drawing:
Delete all occurrences of (6 total) "$R_1$"
Insert --$R_1$--

Page 2, Column 1, drawing:
Delete all occurrences of (2 total) "$R_1$"
Insert --$R_1$--

In the Specification

Columns 1 and 2, Lines 18-35 (drawing):
Delete all occurrences of (8 total) "$R_1$"
Insert --$R_1$--

Columns 5 and 6, Lines 1-21 (drawing):
Delete all occurrences of (8 total) "$R_1$"
Insert --$R_1$--

In the Claims

Column 11, Lines 23-65 - Column 12, Lines 1-21 (drawing):
Delete all occurrences of (8 total) "$R_1$"
Insert --$R_1$--

Column 13, Lines 1-39 (drawing):
Delete all occurrences of (6 total) "$R_1$"
Insert --$R_1$--

Signed and Sealed this
Third Day of March, 2020

Andrei Iancu
*Director of the United States Patent and Trademark Office*

CERTIFICATE OF CORRECTION (continued)
U.S. Pat. No. 10,249,833 B2

Column 14, Lines 1-21 (drawing):
Delete all occurrences of (2 total) "$R_1$"
Insert --R1--